United States Patent [19]

Ng et al.

[11] Patent Number: 4,839,156
[45] Date of Patent: Jun. 13, 1989

[54] STABLE HYDROGEN PEROXIDE DENTAL GEL

[75] Inventors: Shirley M. Ng, Bridgewater; Susan Wieckowski, Iselin, both of N.J.

[73] Assignee: Colgate-Palmolive Company, New York, N.Y.

[21] Appl. No.: 40,439

[22] Filed: Apr. 17, 1987

[51] Int. Cl.$^4$ .................. A61K 7/20; A61K 33/40
[52] U.S. Cl. ............................. 424/53; 424/616
[58] Field of Search ..................... 424/49, 53, 130

[56] References Cited

U.S. PATENT DOCUMENTS

| | | | |
|---|---|---|---|
| 3,639,574 | 2/1972 | Schmolka | 424/78 |
| 3,657,413 | 4/1972 | Rosenthal | 424/81 |
| 3,886,265 | 5/1975 | Evers et al. | 424/49 |
| 4,223,003 | 9/1980 | Scheller | 424/7 |
| 4,226,851 | 10/1980 | Sompayrac | 424/53 |
| 4,273,759 | 6/1981 | Gaffar et al. | 424/49 |
| 4,302,441 | 11/1981 | Muhlemann et al. | 424/48 |
| 4,309,410 | 1/1982 | Gaffar | 424/49 |
| 4,405,599 | 9/1983 | Smigel | 424/53 |
| 4,431,631 | 2/1984 | Clipper et al. | 424/53 |
| 4,476,108 | 10/1984 | Kessler et al. | 424/50 |
| 4,521,403 | 6/1985 | Simon et al. | 424/51 |
| 4,522,805 | 6/1985 | Gordon | 424/52 |
| 4,537,765 | 8/1985 | Gaffar et al. | 424/53 |
| 4,537,778 | 8/1985 | Clipper et al. | 424/53 |
| 4,567,036 | 1/1986 | Simon et al. | 424/51 |
| 4,592,487 | 6/1986 | Simon et al. | 222/94 |
| 4,592,488 | 6/1986 | Simon et al. | 222/94 |
| 4,592,489 | 6/1986 | Simon et al. | 222/94 |
| 4,647,451 | 3/1987 | Piechota | 424/52 |
| 4,684,517 | 8/1987 | Clipper et al. | 424/53 |
| 4,687,663 | 8/1987 | Schaeffer | 424/49 |

OTHER PUBLICATIONS

A. I. El Assay et al, Cosmetics & Toiletries, vol. 91, Sep. 1976, pp. 54–56.

*Primary Examiner*—Shep K. Rose
*Attorney, Agent, or Firm*—Robert L. Stone; Murray M. Grill

[57] ABSTRACT

A stable aqueous hydrogen peroxide dental gel for oral cleaning and anti-gingivitis application having an acid pH of about 4.5-6, comprising about 18-25% by weight of a solid flake or powder poly-oxyethylene polyoxypropylene block copolymer gelling agent, hydrogen peroxide, about 15-40% by weight of a polyethylene glycol humectant, flavor, or sweetening agent such as sodium saccharine, and a nonionic surfactant, as the essential ingredients. Distilled (deionized) water is preferred to prevent minimal contamination.

15 Claims, No Drawings

STABLE HYDROGEN PEROXIDE DENTAL GEL

BACKGROUND AND PRIOR ART

The present invention relates to the formation of a cosmetic and chemically stable aqueous hydrogen peroxide-containing dental gel having an acid pH of about 4.5–6, comprising a compatible system of specified amounts of specific dental components.

Until now, it has been difficult to formulate a cosmetic and chemically stable hydrogen peroxide gel with appropriate thickening/gelling agents, humectants, surfactants and flavor for oral application. However, after extensive experimentation on various mixtures of components in the hydrogen-peroxide dental gel product, a compatible system of water, polyoxyethylene-polyoxypropylene block copolymer gelling agent, polyethylene glycol humectant, nonionic surfactant, sweetening agent and flavor has been discovered. This dental product is in the form of a stable rigid gel having improved chemical and cosmetic stability and improved taste.

It has long been recognized in the art that hydrogen peroxide and other peroxygen-containing agents are effective in curative and/or prophylactic treatments with respect to cleaning caries dental plaque, gingivitis, periodontitis, mouth odor, tooth stains, recurrent aphthous ulcers, denture irritations, orthodontic appliance lesions, postextraction and postperiodontal surgery, traumatic oral lesions and mucosal infections, herpetic stomatitis and the like. Peroxide-containing agents in the oral cavity exert a chemomechanical action generating thousands of tiny oxygen bubbles produced by interaction with tissue and salivary enzymes. Peroxide mouthrinses and other oral preparations prevent colonization and multiplication of anaerobic bacteria known to be associated with periodontal disease. Peroxygen-containing gels or pastes are indicated and/or desirable where it is required to selectively treat areas for more than a few seconds, such gels and pastes tending to remain at the site of application for a time sufficient for the peroxide to manifest its maximum effectiveness.

It is also known that most peroxy compounds such as hydrogen peroxide in oral compositions tend to be unstable in storage due to incompatibility with, or interaction with, other common ingredients in the composition, and lose the capacity to release active or nascent oxygen over relatively short periods of time. This adversely affects both the chemical stability of the composition as well as the cosmetic stability of the final product, particularly in the gel product containing hydrogen peroxide.

The prior art has attempted to solve said problems by using a variety of stabilizers for dental compositions in assorted forms such as tablets, chewing gum, mouthwashes, toothpastes or powder containing a hydrogen peroxide, as shown in U.S. Pat. No. 4,226,851 wherein is disclosed an aqueous mouthwash containing hydrogen peroxide, flavor, zinc chloride and water soluble Vitamin E which stabilizes the hydrogen peroxide in the mouthwash. U.S. Pat. No. 4,302,441 discloses solid oral products (tablets and chewing gum) containing urea hydrogen peroxide in gum bases such as jelutong, rubber latex, vinylite resins, etc., and in methyl, ethyl and sodium carboxymethyl cellulose carriers, free of glycerol, also containing sweeteners such as sodium saccharinate, xylitol, sorbitol, and mannitol and flavors. U.S. Pat. No. 4,476,108 discloses an admixture of a peroxidase, a peroxide and a donor molecule such as phenylethylamine, tyrosine, tryptophan, benzoic acid, salicylic acid, hydroquinone, dihydrophenyl-alanine, vanillan and paraaminobenzoic acid, in a carrier such as water (mouthwash) or in the form of a paste, gel or powder. U.S. Pat. No. 4,431,631 discloses an aqueous oral solution containing hydrogen peroxide, glycerine and/or sorbitol humectant, 0.5–3% pluronic-type surfactant, polyoxyethylenated sorbitol monofatty acid ester surfactant, sweetener and flavor.

The prior art also discloses dental compositions containing a hydrogen peroxide and an additional component to effect stabilization, such as ascorbic acid in U.S. Pat. No. 3,886,265, wherein is disclosed tablets, lozenges, chewing gum or an aerosol or spray form containing a peroxide such as hydrogen peroxide and an ene-diol compound such as ascorbic acid, effective against bad breath.

U.S. Pat. No. 4,521,403 discloses a method of controlling and treating periodontal diseases by washing the teeth with an aqueous or aqueous alcoholic solution of a hydrogen peroxide and a povidone-iodine complex (complex of iodine with 1-vinyl-2-pyrrolidone polymers). These two ingredients are mixed only prior to use U.S. Pat. No. 4,592,487 discloses an antiplaque dentifrice in the form of a toothpaste or gel containing the two components, a peroxide and povidone-iodone complex, each separately mixed with conventional dentifrice components, and kept separated until admixed and dispensed from a special dual compartment container/mixer/dispenser device.

U.S. Pat. No. 4,592,488 discloses an oral composition containing an iodophor or quaternary ammonium compound and a peroxy compound such as hydrogen peroxide in the form of an aqueous or aqueous alcoholic solution prior to combining the two components into an oral mouthwash.

U.S. Pat. No. 4,592,489 discloses a two-part container for dispensing an oral mouthwash containing the povidone-iodine complex solution separate from the hydrogen peroxide solution and mixing prior to dispensing.

Dental compositions containing other oxidizing agents in lieu of the hydrogen peroxide are also disclosed in the prior art.

U.S. Pat. No. 4,522,805 and 4,567,036 disclose a stable toothpaste to aid in controlling periodontal disease, containing an oxidizing agent such as carbamide peroxide (urea peroxide) which dissociates into urea and hydrogen peroxide in the oral cavity, in a paste carrier comprising an anionic detergent, sorbitol and glycerin humectant and a thickening agent such as gum tragacanth, sodium alginate or sodium carboxymethyl cellulose.

U.S. Pat. No. 4,405,599 discloses toothpaste containing calcium peroxide and sodium perborate oxidizing agents; dicalcium phosphate, calcium carbonate and magnesium carbonate cleaning agents; sorbitol humectant; cornstarch and cellulose gum thickening agents, and an anionic detergent.

U.S. Pat. No. 4,223,003 discloses a toothpaste or toothpowder containing peroxide-containing substances such as magnesium peroxide and conventional dentifrice components.

U.S. Pat. No. 4,537,765 discloses a toothpaste having a pH of 9.2–10.5 containing a peroxydiphosphate salt, a polyethylene glycol humectant, a thickener such as colloidal silica, carboxyvinyl polymer, cellulose gums, or hectorite; a polishing agent such as silica or hydrated alumina and anionic or nonionic surfactants such as Pluronic F108.

However, none of the aforesaid patents disclose the preparation of hydrogen peroxide dental gels containing the essential specific components of a polyethylene glycol humectant, a non-ionic surfactant, flavor, and a polyoxyethylene polyoxypropylene block copolymer thickening agent in the formation of a stable dental gel.

The prior art also discloses processes of preparing other peroxide gels as shown in U.S. Pat. No. 3,657,413 and the article by Assay et al, "Stability of Hydrogen Peroxide in Certain Pharmaceutical Gels" Cosmetics and Toiletries, 54–56, 91, September 1976. The patent discloses a clear gel comprising urea peroxide, glycerol, a carboxypolymethylene polymer and flavor; prepared by dispersing the polymer into the glycerol with high speed stirring at reduced pressure and then dissolving the urea peroxide and other ingredients in the thickened polymer/glycerol solution yielding a viscous gel. The article discloses methyl cellulose gels for treating surface cuts, bleaching hair and for deodorant purposes containing 0.1% oxine as stabilizer for the hydrogen peroxide; prepared by dispersing the methyl cellulose in water using an electric stirrer and then neutralizing with tri-ethanolamine to yield a gel; or dispersing in hot water until well hydrated, refrigerating until solidified and stirring until a gel is obtained, adding the stabilizer oxine to the gel, followed by the addition of the hydrogen peroxide. Other stabilizers which are not as effective as oxine include hexamine, benzoic acid or urea.

Hydrogen peroxide gels containing polyoxyethylene polyoxypropylene block copolymers as the gelling/thickening agent is disclosed in U.S. Pat. Nos. 3,639,574 and 4,537,778. The former patent discloses a stable hydrogen peroxide gel for use in hair bleaching and treating surface cuts, using polyoxyethylene polyoxypropylene block copolymers as gelling agents in amounts of 22–79% of the total compositions.

This is not a dental gel, does not contain the polyethylene glycol humectant, sodium saccharine sweetener, or flavor which are essential ingredients in the dental gel. The latter patent discloses an aqueous oral preparation which may be in the form of a mouthrinse, a paste or a gel containing hydrogen peroxide, a flavor and 20% of a thickener (for the gel form), 1–20% polyhydric alcohols such as glycerol and sorbitol, 0.1–10% nonionic surfactants such as Tweens (polysorbate) and/or Pluronics. The Pluronic (F127) is the preferred gelling agent (5–50%). There is no mention of polyethylene glycol humectant which is the exclusive effective humectant used in this formulation.

Moreover, the prior art does not disclose a cosmetic and chemically stable aqueous hydrogen peroxide dental gel having a pH of 4.5–6.0 containing as the essential ingredients, a polyoxyethylene polyoxypropylene block copolymer gelling agent, a polyethylene glycol humectant, a nonionic surfactant, sweetener, i.e. sodium saccharin and flavor, in specified proportions.

SUMMARY OF THE INVENTION

It has now been found that an aqueous hydrogen peroxide dental gel can be stabilized in the presence of polyethylene glycol, sodium saccharin, nonionic surfactant and flavor when using a polyoxyethylene polyoxypropylene block copolymer (Pluronics) at a level of about 18–25% by weight as the gelling agent. The Pluronic gelling agents are compatible with the aqueous hydrogen peroxide, whereas the natural gums derived from organic material such as the alginate, methyl cellulose and the like are degraded by the hydrogen peroxide, resulting in unstable gels. Similarly, synthetic organic polymers such as polyvinylpyrrolidone form a stringy gel, which is not the clear, homogeneous rigid gel in accordance with present novel dental gel product. The presence of stabilizers such as sodium stannate, sodium pyrophosphate, oxine EDTA and calcium disodium EDTA have been found to be unnecessary and undesirable, because their presence provide no advantages to the composition. As a matter of fact their presence tend to adversely affect the chemical stability of the $H_2O_2$. The combination of polyethylene glycol humectant and the block copolymer gelling agent has been found to yield a more stable rigid gel than a gel prepared with the block copolymer gelling agent in the absence of the polyethylene glycol. The use of nonionic surfactants have been found to have acceptable stability in an aqueous peroxide environment. The anionic surfactants do not have acceptable stability in the presence of hydrogen peroxide.

Accordingly, a primary object of the present invention is to formulate a cosmetically and chemically stable hydrogen peroxide dental gel having a pH of about 4.5–6.0 containing a polyoxyethylene polyoxypropylene block copolymer gelling agent in amounts of about 18–25% by weight of the composition which is compatible with the $H_2O_2$.

Another object of this invention is to provide a cosmetically stable $H_2O_2$-polyoxyethylene polyoxypropylene block copolymer gel containing polyethylene glycol humectant which is compatible with the other dental ingredients.

Still another object of this invention is to provide a cosmetically and chemically stable aqueous $H_2O_2$ dental gel having improved taste, containing a compatible formulation of the block copolymer gelling agent, polyethylene glycol humectant, nonionic surfactant, flavor and sweetening agent, such as sodium saccharine.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

To achieve the foregoing and other objects and in accordance with the present invention, as embodied and broadly described herein, the novel stable aqueous hydrogen peroxide dental gel of this invention comprises about 1.5–3.5% by weight $H_2O_2$ as the sole chemically active agent, about 18–25% by weight of a solid flake or powder polyoxyethylene polyoxypropylene block copolymer gelling agent (Pluronic), about 15–40% by weight of a polyethylene glycol humectant, a nonionic surfactant, sweetener and flavor, said gel having an acid pH of about 4.5–6. Sodium saccharin is the preferred sweetener. The water content in the gel constitutes about 30–60% by weight of the oral composition. Distilled or deionized water is preferred to prevent minimal contamination.

The hydrogen peroxide formulation of present invention contains an effective amount of hydrogen peroxide for oral anti-gingivitis application, preferably about 1.5–3.5% by weight of the composition. Hydrogen peroxide is usually supplied as 30–35% aqueous solutions containing 1.5-3.5% active ingredient. The hydrogen peroxide is stable in the presence of polyethylene glycol, sodium saccharin, nonionic surfactant, flavor, and the Pluronic gelling agent.

An essential ingredient in present H₂O₂ gel dentifrice is a compatible peroxide-stable thickening and gelling agent which is a polyoxyethylene polyoxypropylene block copolymer in an amount of about 18-25% by weight of the composition. Amounts less than about 18% provide insufficient thickening for the hydrogen peroxide gel dentifrice; and amounts greater than about 25% are difficult to formulate. Useable agents include Pluronic Polyols which are nonionic and may be represented by the formula

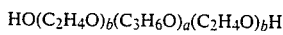

$$HO(C_2H_4O)_b(C_3H_6O)_a(C_2H_4O)_bH$$

wherein a is an integer such that the hydrophobic base represented by $(C_3H_6O)$ has a molecular weight of about 2750 to 4000, b is an integer such that the hydrophilic portion (moiety) represented by $(C_2H_4O)$ constitutes about 70-80% by weight of the copolymer. Pluronic Polyols of the F (solid flake or powder) type, with a hydrophobe of M.W. of about 2750 to 4000 and with from 70 to 80% hydrophilic polyoxyethylene groups form a gel at 18-25% by weight of the H₂O₂/Pluronic gel formulation. Examples of suitable Pluronic compounds are Pluronic F88, F98, F108 and F127. The most preferred gelling agent is Pluronic F127, which has a molecular weight of 4000 and contains 70% of the hydrophilic polyoxyethylene moiety. It is most preferably employed in the gel dentifrice in an amount of about 18-19% by weight.

The completed 12 weeks accelerated temperature aging data of aqueous Pluronic-H₂O₂ gels with and without stabilizers are acceptable both cosmetically and chemically, except for a formula which contained sodium lauryl sulfate, anionic surfactant. Sodium stannate, sodium pyrophosphate, oxine, phosphoric acid and disodium EDTA are effective in stabilizing aqueous H₂O₂ systems. However, results from the active oxygen data suggest that the system which contains no stabilizers appears to be the best chemically. 90% of H₂O₂ activity was available after 6 weeks of cosmetic aging (accelerated temperature aging). Rheological results indicate that the Pluronic gels are quite stable in terms of yield point and resolidification points. The gels do not thicken up with time and after 12 weeks at 100° F. the yield point only decreased by 10% which is within experimental error.

Another essential ingredient in the H₂O₂ gel formulation of present invention is the polyethylene glycol humectant which is compatible with the hydrogen peroxide, the nonionic surfactant, flavor and the Pluronic gelling agent. Polyethylene glycols known by the trademark CARBOWAX are nonionic polymers of ethylene oxide having the general formula:

$$HOCH_2(CH_2OCH_2)_nCH_2OH$$

wherein n represents the average number of oxyethylene groups. The Carbowax polyethylene glycols are designated by a number such as 400, 600, etc. which represents the average molecular weight. The average molecular weight of the polyethylene glycols used herein is about 200-1000, preferably 400-600 and most preferably 600. The polyethylene glycols 200, 300, 400 and 600 are clear viscous liquids at room temperature. They are less hygroscopic than glycerin and simple glycols, are water soluble and form a clear aqueous solution. The polyethylene glycols provide a different and better feel and taste to the dental product than the glycerin or sorbitol. It has been found that the polyethylene glycol humectant also aids in making a superior stable rigid Pluronic H₂O₂ gel to the gel with glycerine. The polyethylene glycol humectant constitutes about 15-40% by weight of the H₂O₂ formulation.

Another essential ingredient in the aqueous H₂O₂ gel formulation of this invention is the nonionic surfactant which is compatible with the H₂O₂ and is peroxide-stable. The nonionic surfactant serves as a solubilizing, dispersing, emulsifying and wetting agent and is especially effective in solubilizing the flavor. A particularly useful nonionic surfactant is a water soluble polyoxyethylene monoester of sorbitol with a $C_{10}$ to $C_{18}$ fatty acid, known under the Tween trademark. The tween surfactants are mixtures of $C_{10-18}$ fatty acid esters of sorbitol (and sorbitol anhydrides), consisting predominantly of the monoester, condensed with about 10-30, preferably about 20, moles of ethyleneoxide. The fatty acid (aliphatic hydrocarbon-monocarboxylic acid) may be saturated or unsaturated, e.g. lauric, palmitic, stearic, oleic acids. Polysorbate 20 (e.g. Tween 20) is especially preferred, and is commonly referred to as polyoxyethylene (20) sorbitan monolaurate. The nonionic surfactant constitutes about 0.5 to 5.0% by weight and preferably 0.5 to 3% by weight of the gel composition.

Another essential ingredient in present aqueous H₂O₂ gel dentifrice is an effective flavoring amount of a flavor compatible and stable with the hydrogen peroxide. The flavor ingredient constitutes about 0.5-2% by weight. Suitable flavoring constituents are flavoring oils, e.g., oils of spearmint, peppermint, wintergreen, sassafras, clove, sage, eucalyptus, marjoram, cinnamon, and methyl salicylate, and menthol.

A sweetening material is preferably also employed as a complement to the flavoring material. Suitable sweetening agents are water soluble and include sodium saccharin, sodium cyclamate, xylitol, perillartine, D-tryptophan, aspartame, dihydrochalcones and the like, in concentrations of about 0.01 to 1.0% by weight. Sodium saccharine is preferred.

The pH of the H₂O₂ gel dentifrice of the invention ranges from about 4.5 to 6. The pH of the prepared composition is generally adjusted to about 5.0 to 6.0 with an appropriate acid such as phosphoric acid or citric acid, and the pH decreases to approximately 4.5 after 12 weeks accelerated aging. This acidic pH affords greater stability to the gel product of present invention, the lower the pH the greater the stability.

The hydrogen peroxide gel dentifrice of this invention may also contain conventional additional ingredients such as coloring or whitening agents, or preservatives such as sodium benzoate, in minimal amounts of up to 5% by weight and preferably up to 1%, provided they do not interfere with the chemical and cosmetic (physical) stability properties of the finished product.

It has been found that only by utilizing the specific combination of ingredients of nonionic surfactant, polyethylene glycol humectant, polyoxyethylene polyxoypropylene block copolymer (Pluronics) gelling agent, sweetening agent and flavor, can a cosmetic and chemically stable aqueous hydrogen peroxide gel dentifrice having improved taste, be formulated.

The rigid stable hydrogen peroxide dental gel of this invention may be prepared by dissolving the hydrogen peroxide, saccharin and the Pluronic gelling agent in the formula amount of water, preferably deionized water (to prevent even minimal contamination) heated to a temperature of about 32°–32.5° C. by mixing in any suitable mixer, such as a Ross mixer, under vacuum for about 30 minutes until a gel is formed. The flavor, nonionic surfactant and polyethylene glycol are added to the gel and mixed under vacuum for about another 14–30 minutes. A rigid, clear, homogeneous stable gel dentifrice product is obtained which may be acidified to a pH of about 5–6 with phosphoric acid or citric acid, if necessary. The final product may be packaged in any suitable container compatible with hydrogen peroxide, such as plastic or metal tubes; or in a dual compartment container or kit with a bicarbonate dentifrice. This is the preferred method of preparation because it is a faster and more simple method of preparation.

Another method of preparing the hydrogen peroxide dental gel of present invention comprises dissolving the Pluronic gelling agent in the formula amount of water cooled to about 4°–10° C., followed by the addition of the hydrogen peroxide, and the saccharin in the formation of a water phase; separately emulsifying the flavor with the nonionic surfactant in a small amount of water to form an emulsion; adding the humectant and the above emulsion to the Pluronic water phase and mixing under vacuum until a clear, homogeneous gel is formed.

The final product is a rigid ringing gel which may be described as gels that have a firm jelly-like consistency; that is, when said gel is packed in a jar type container, and the sides of said container are tapped lightly, the gel vibrates but retains its original configuration. The dental gel product of present invention is a dentifrice and not a mouthrinse, and will dissolve in the oral cavity only upon brushing.

In the practice of this invention to promote oral hygiene, the gel dentifrice according to this invention is applied regularly to dental enamel by brushing the teeth for 30–90 seconds at least once daily.

DETAILED DESCRIPTION OF THE INVENTION

The following examples are further illustrative of the nature of the present invention, but it is understood that the invention is not limited thereto. The compositions are prepared in the usual manner and all amounts and proportions referred to herein and in the appended claims are by weight unless otherwise indicated.

EXAMPLE 1

| Ingredients | % |
| --- | --- |
| Deionized Water | 42.10 |
| Pluronic F127 | 25.00 |
| Na Saccharin | 0.20 |
| $H_2O_2$ (30% aqueous Solution) (3% A.I.) | 10.00 |
| Polyethylene Glycol (mol. wt. 600) | 15.00 |
| Deionized Water | 5.00 |
| Tween 20' | 1.20 |
| Flavor | 1.50 |
| pH - 6.5 | |

'polyoxyethylene (20) sorbitan monolaurate.

The formula amount of deionized water is heated to about 32.2° C. and mixed together with the saccharin and hydrogen peroxide, and placed in a Ross mixer, the surface is covered completely with the Pluronic compound and mixed under vacuum at speed 3 for ½ hour. The Tween, flavor and 5% deionized water mixture and the polyethylene glycol are added to the aqueous phase in the Ross mixer and mixed under vacuum at Speed 3 for about 15–25 minutes. A clear and homogeneous rigid gel is obtained having a pH of 6.5, which may be adjusted to a pH of 5–6, with 10% phosphoric acid or citric acid. A stable rigid gel is obtained having excellent storage stability with respect to flavor, color, appearance, taste and peroxy content.

After twelve weeks of accelerated aging, the pH decreases to approximately 4.5. The data show less than 10.0% loss of active oxygen. This formulation has 2.9% active oxygen initially and after aging 9 weeks at 433° C. has a 2.8% active oxygen.

EXAMPLE 2

| Ingredients | % |
| --- | --- |
| Deionized Water | 48.50 |
| Pluronic F127 | 20.00 |
| Na Saccharin | 0.20 |
| $H_2O_2$ (35% Aqueous solution) (3.01% A.I.) | 8.60 |
| Polyethylene glycol (mol. wt. 600) | 15.00 |
| Deionized Water | 5.00 |
| Tween 20 | 1.20 |
| Flavor | 1.50 |

The dental hydrogen peroxide gel formulation is prepared by the same procedure outlined in Example 1. The resultant product also exhibits excellent storage stability and is in the form of a stable rigid clear gel.

EXAMPLE 3

Example 2 is repeated except that polyethylene glycol (400 mol. wt.) is substituted for the polyethylene glycol (600 M.W.). The end product is equally effective against gingivitis related bacteria and also possess excellent chemical and cosmetic stability properties. This product has 2.76% active oxygen initially, and after aging 9 weeks at 43.3° C. has 2.59% active oxygen.

EXAMPLE 4

Example 2 is repeated except that the sodium saccharin is omitted and the deionized water content is increased to 48.77%. The omission of the sodium saccharin had no adverse affects on the final hydrogen peroxide dental gel.

EXAMPLE 5

Example 1 is repeated except that 18% Pluronic F127 is used instead of 25% and the water content is increased to 49.10%. The resultant product possesses excellent chemical and cosmetic stability similarly to Example 1.

This invention has been disclosed with respect to preferred embodiments, and various modifications and variations thereof obvious to those skilled in the art are to be included within the spirit and purview of this application and the scope of the appended claims.

We claim:

1. A rigid, clear, homogeneous stable aqueous hydrogen peroxide dental gel consisting essentially of about 1.5–3.5% by weight hydrogen peroxide as the sole chemically active agent, about 18–25% by weight of a solid flake or powder polyoxyethylene-polyoxypropylene block copolymer gelling agent, about 15–40% by weight of a polyethylene glycol humectant, a nonionic surfactant, and a flavor, said gel having an acid pH of about 4.5 to 6.

2. The dental gel according to claim 1 including a sweetening material.

3. The dental gel according to claim 2 wherein the sweetening material is sodium saccharin.

4. The dental gel according to claim 1, wherein the gelling agent is a solid polyoxyethylene polyoxypropylene copolymer wherein the polyoxypropylene hydrophobic moiety has a molecular weight of about 2250 to 4000 and the hydrophilic polyoxyethylene moiety constitutes about 70-80% of the copolymer.

5. The dental gel according to claim 4 wherein the gelling agent constitutes about 18-19% by weight of the composition.

6. The dental gel according to claim 1, wherein the polyethylene glycol humectant has an average molecular weight of about 200-1000.

7. The dental gel according to claim 6, wherein the polyethylene glycol has an average molecular weight of about 400-600.

8. The dental gel according to claim 1, wherein the nonionic surfactant constitutes about 0.5-5% by weight.

9. The dental gel according to claim 8, wherein the nonionic surfactant is a polyoxyethylene monoester of sorbitol with a $C_{10}$ to $C_{18}$ fatty acid.

10. The dental gel according to claim 1, wherein the aqueous content constitutes about 30-60% by weight of deionized water.

11. A dental gel according to claim 1, wherein the nonionic surfactant constitutes about 0.5-2% by weight and the flavor content is about 0.5-2% by weight.

12. A dental gel according to claim 9, wherein the nonionic surfactant is polyethylene (20) sorbitan monolaurate.

13. A dental gel according to claim 4, wherein the hydrophobic moiety of the gelling agent has a molecular weight of 4000 and the hydrophilic moiety constitutes 80% by weight of the copolymer.

14. A process of preparing the hydrogen peroxide gel defined in claim 1, which comprises dissolving the hydrogen peroxide, sodium saccharin and the copolymer gelling agent in the formula amount of deionized water heated to about 32°-32.5° C. and mixing under vacuum for about thirty minutes to form a gel; adding the polyethylene glycol, flavor and nonionic surfactant to the gel and mixing under vacuum for about 15-30 minutes until a clear, homogeneous, rigid gel is obtained.

15. A process of preparing the hydrogen peroxide gel defined in claim 2, which comprises forming an aqueous phase consisting of the gelling agent, the hydrogen peroxide and the sweetening material by dissolving the block copolymer gelling agent in the formula amount of water cooled to about 4°-10° C. and adding thereto the hydrogen peroxide and the sweetening material; separately emulsifying the flavor with the nonionic surfactant in a small amount of water to form an emulsion; adding the humectant and said emulsion to said aqueous phase, and mixing under vacuum until a clear homogeneous, rigid gel is formed.

* * * * *